United States Patent
Buerk et al.

(10) Patent No.: US 10,729,513 B2
(45) Date of Patent: Aug. 4, 2020

(54) DENTAL TREATMENT OR EXAMINATION SYSTEM AND ALSO METHOD FOR THE OPERATION OF SUCH A SYSTEM

(71) Applicant: KALTENBACH & VOIGT GMBH, Biberach (DE)

(72) Inventors: Richard Buerk, Alberweiler (DE); Johannes Sauter, Mittelbuch (DE)

(73) Assignee: KALTENBACH & VOIGT GMBH, Biberach (DE)

( * ) Notice: Subject to any disclaimer, the term of this patent is extended or adjusted under 35 U.S.C. 154(b) by 0 days.

(21) Appl. No.: 15/335,211

(22) Filed: Oct. 26, 2016

(65) Prior Publication Data

US 2017/0119495 A1 May 4, 2017

(30) Foreign Application Priority Data

Oct. 29, 2015 (EP) .................................... 15192143

(51) Int. Cl.
*A61C 1/00* (2006.01)
*A61G 15/14* (2006.01)
(Continued)

(52) U.S. Cl.
CPC .......... *A61C 1/0015* (2013.01); *A61C 1/0007* (2013.01); *A61G 15/14* (2013.01);
(Continued)

(58) Field of Classification Search
CPC .... A61C 1/0015; A61C 1/0007; G61H 40/63; A61G 15/14; G01R 27/2605; G16H 40/40; G16H 40/63
See application file for complete search history.

(56) References Cited

U.S. PATENT DOCUMENTS 5,873,717 A * 2/1999 Behringer ............ A61C 1/0015
433/101
5,931,669 A * 8/1999 Fornoff ................ A61C 1/0007
433/28
(Continued)

FOREIGN PATENT DOCUMENTS

DE 2712734 9/1978
DE 4409862 9/1995
(Continued)

OTHER PUBLICATIONS

Translation of DE 19702996 which is U.S. Pat. No. 5,873,717 (Year: 1998).*
(Continued)

*Primary Examiner* — Heidi M Eide
(74) *Attorney, Agent, or Firm* — Michael Best & Friedrich LLP

(57) ABSTRACT

A dental treatment or examination system having a plurality of dental instruments and a supply unit coupled to the dental instruments. The system includes means to identify the contact of a selected dental instrument from the plurality of dental instruments by a human hand and initializes, based upon an identified contact of the selected dental instrument, the supply unit for an operation of the instrument. When the selected instrument is contacted by a human hand, the supply unit may automatically make available activation or parameterization options for the selected instrument and/or suitable cleaning media available to an operator of the selected instrument.

10 Claims, 5 Drawing Sheets

(51) Int. Cl.
  *G01R 27/26* (2006.01)
  *G16H 40/63* (2018.01)
  *G16H 40/40* (2018.01)
(52) U.S. Cl.
  CPC ......... *G01R 27/2605* (2013.01); *G16H 40/40* (2018.01); *G16H 40/63* (2018.01)

(56) References Cited

U.S. PATENT DOCUMENTS

| | | | | |
|---|---|---|---|---|
| 6,113,395 | A * | 9/2000 | Hon | G09B 23/28 |
| | | | | 434/262 |
| 2004/0059197 | A1* | 3/2004 | Yamashita | A61B 5/0002 |
| | | | | 600/300 |
| 2010/0069940 | A1* | 3/2010 | Miller | A61B 17/320068 |
| | | | | 606/169 |
| 2016/0367326 | A1* | 12/2016 | Schrock | A61C 1/0007 |

FOREIGN PATENT DOCUMENTS

| | | | | |
|---|---|---|---|---|
| DE | 19508481 | | 9/1996 | |
| DE | 19702996 | | 5/1998 | |
| DE | 10139020 | | 3/2003 | |
| DE | 102008025543 | | 12/2009 | |
| EP | 0017318 | | 10/1980 | |
| EP | 2915502 | * | 9/2015 | ............... A61C 1/00 |
| WO | 2010/051080 | | 5/2010 | |

OTHER PUBLICATIONS

Translation of EP2915502 which is US2016/0367326 (Year: 2015).*
EP15192143.4 Extended European Search Report dated Apr. 7, 2016 (7 pages).

* cited by examiner

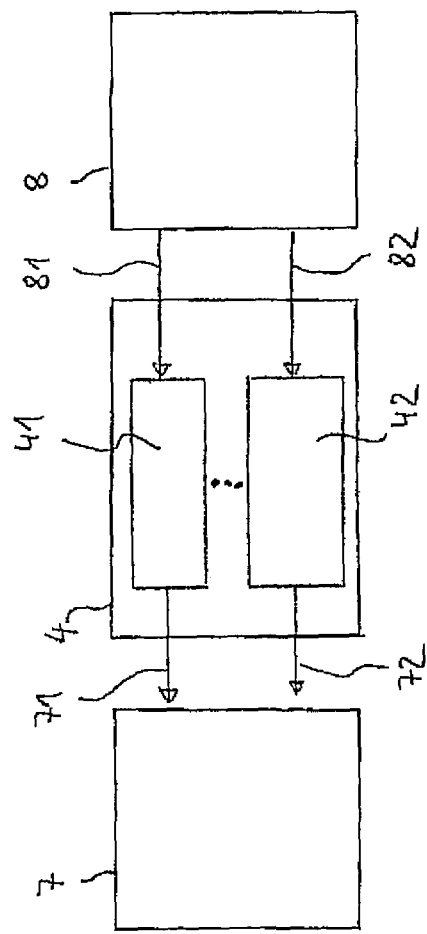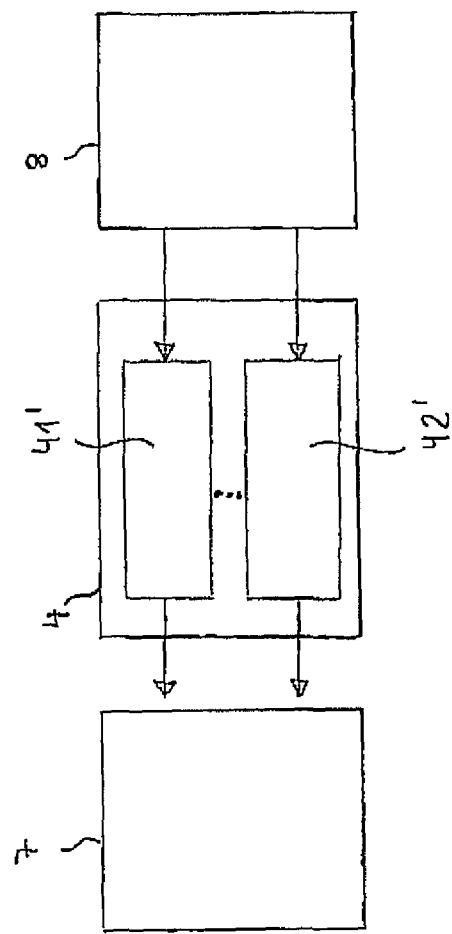

Instrument n:

Parameter A

Parameter B

Parameter C

Actual value X

Actual value Y

Fig. 4b

Instrument 1:

Parameter 1

Parameter 2

Actual value 1

Fig. 4a

DENTAL TREATMENT OR EXAMINATION SYSTEM AND ALSO METHOD FOR THE OPERATION OF SUCH A SYSTEM

The invention relates to a dental treatment or examination system and also to a method for the operation of such a system.

A dental treatment or examination system is known from the prior art in the form of a dental treatment unit. Such a dental treatment unit in accordance with the prior art comprises a so-called dentist's element with a plurality of quiver-like instrument-holders for dental instruments. In order to identify that one of these instruments has been removed from its instrument-holder or to select one of these instruments in order to initialize its activation, use is made of a microswitch, arranged in the region of the instrument-holder, a reed contact or a pressure switch or a separate preselection switch. Integration of such a microswitch, reed contact or pressure switch into the treatment unit is linked with a comparatively high level of outlay. A separate preselection switch involves an operation that is comparatively uncomfortable.

If a parameter, for example a motor speed, is to be programmed for one of the instruments, to this end the relevant instrument must first be selected or preselected either by removing the instrument from its instrument-holder or by means of a menu indicated on a display. Both require an increased level of outlay in terms of operation.

The underlying object of the invention is to specify a corresponding improved dental treatment or examination system; in particular the system, with a simple possibility of production, is to offer improved operating comfort. Moreover, a corresponding method for operating a dental treatment or examination system is to be specified.

This object is achieved in accordance with the invention with the subject matter mentioned in the independent claims. Particular embodiments of the invention are specified in the dependent claims.

In accordance with the invention, a dental treatment or examination system is provided that comprises a plurality of treatment or examination instruments and also a supply unit coupled to the plurality of treatment or examination instruments. In this connection, the system has means to identify the contact of a selected instrument from the plurality of treatment or examination instruments, wherein, as a function of an identified contact of the selected treatment or examination instrument, the supply unit is initialized for an operation of the selected treatment or examination instrument. This initialization can, for example, include the making available of activation or parameterization options for the selected treatment or examination instrument and/or of media, such as, for example, air or water. The electrical connection of the selected treatment or examination instrument to a power output of a control unit can also represent initialization for the purposes of the invention.

Using the means to identify the contact it is thus possible to achieve a situation where the supply unit automatically makes available, for example, the activation or parameterization options for the relevant treatment or examination instrument, that is, the treatment or examination instrument that has been selected by the contact, and/or the suitable media without more extensive manipulation on the part of the user of the treatment or examination system being required therefor. As a result, the operation is facilitated.

The means for identifying the contact in this connection preferably comprise at least one capacitive sensor. A capacitive sensor is suitable particularly for contact-identification.

Moreover, in this way it is possible to achieve a situation where in this case no corresponding microswitch, reed contact or pressure switch or the like is required. This is advantageous in particular with respect to a facilitated and cost-effective possibility of production of the system.

The treatment or examination instrument is preferably configured in this connection in such a way that the means for identifying the contact evaluate the capacitive coupling-in to the housing of the contacted or selected treatment or examination instrument—or instrument for short—or to lines thereof, wherein the capacitive coupling-in is ascertained in particular by measuring ripple or interference voltages. As an alternative to this, the configuration can be such that the means for identifying the contact evaluate a change in capacitance of the treatment or examination instrument.

The means for identifying the contact preferably comprise an evaluation unit that is arranged in the supply unit and is connected to the treatment or examination instruments by way of a sensor line. In this connection, the sensor line is, furthermore, preferably formed by a current-supply line for the treatment or examination instruments.

The means for identifying the contact of a treatment or examination instrument can, if applicable, also be integrated into the instrument.

The treatment or examination system is preferably configured in such a way that identification of the contact of the selected treatment or examination instrument is carried out merely in a non-activated state of the treatment or examination instruments available for selection. In this way, it is possible to reduce the risk of interrupting the supply of media whilst working with the instrument.

The configuration is, furthermore, preferably such that the supply unit has a display or is connected to a display on which a presentation of operating parameters of the selected treatment or examination instrument is effected, wherein the presentation is effected as a function of the identification of the contact of the selected treatment or examination instrument. In this way, it is possible to avoid a situation where in order to set operating parameters the relevant treatment or examination instrument must first be chosen or selected by means of another manipulation, for example by means of manipulation of a preselection switch.

In accordance with a further aspect of the invention a method is provided for operating a dental treatment or examination system having a plurality of treatment or examination instruments and also having a supply unit coupled to the plurality of treatment or examination instruments. In this connection, a contact of the treatment or examination instruments is monitored and as a function of an identified contact of one of the treatment or examination instruments the supply unit is initialized for an operation of the selected treatment or examination instrument. As a result, a situation can be achieved where the selection, that is, the choice of the relevant instrument is effected solely by means of the contact of this instrument. The operation of the system is facilitated in this way.

The initialization in accordance with the invention can include, for example, the making available of activation or parameterization options for the selected treatment or examination instrument and/or of media, such as, for example, air or water. The electrical connection of the selected treatment or examination instrument to a power output of a control unit can also be effected in the course of the initialization in accordance with the invention.

In this case, at least one capacitive sensor is preferably used to identify the contact of the one of the treatment or examination instruments.

Furthermore, in this connection in order to identify the contact, the capacitive coupling-in to the housing of the relevant treatment or examination instrument or to lines thereof is preferably evaluated, wherein the capacitive coupling-in is ascertained in particular by measuring ripple or interference voltages. As an alternative to this, a change in capacitance of the relevant treatment or examination instrument is evaluated in order to identify the contact.

An identification of the contact of the one of the treatment or examination instruments is preferably carried out merely in a non-activated state of the relevant treatment or examination instrument.

The supply unit preferably has a display or is connected to a display on which a presentation of operating parameters of the one of the treatment or examination instruments is effected, wherein the presentation is effected as a function of the identification of the contact of the relevant treatment or examination instrument.

The invention is explained in greater detail in the following with the aid of an exemplary embodiment and with reference to the drawings, in which:

FIG. 2a shows a sketch of a possible embodiment of the means for identifying the contact;

FIG. 2b shows a sketch of a further possible embodiment of the means for identifying the contact;

FIGS. 4a, 4b show sketches of a possible presentation on the display; and

Figure 1:
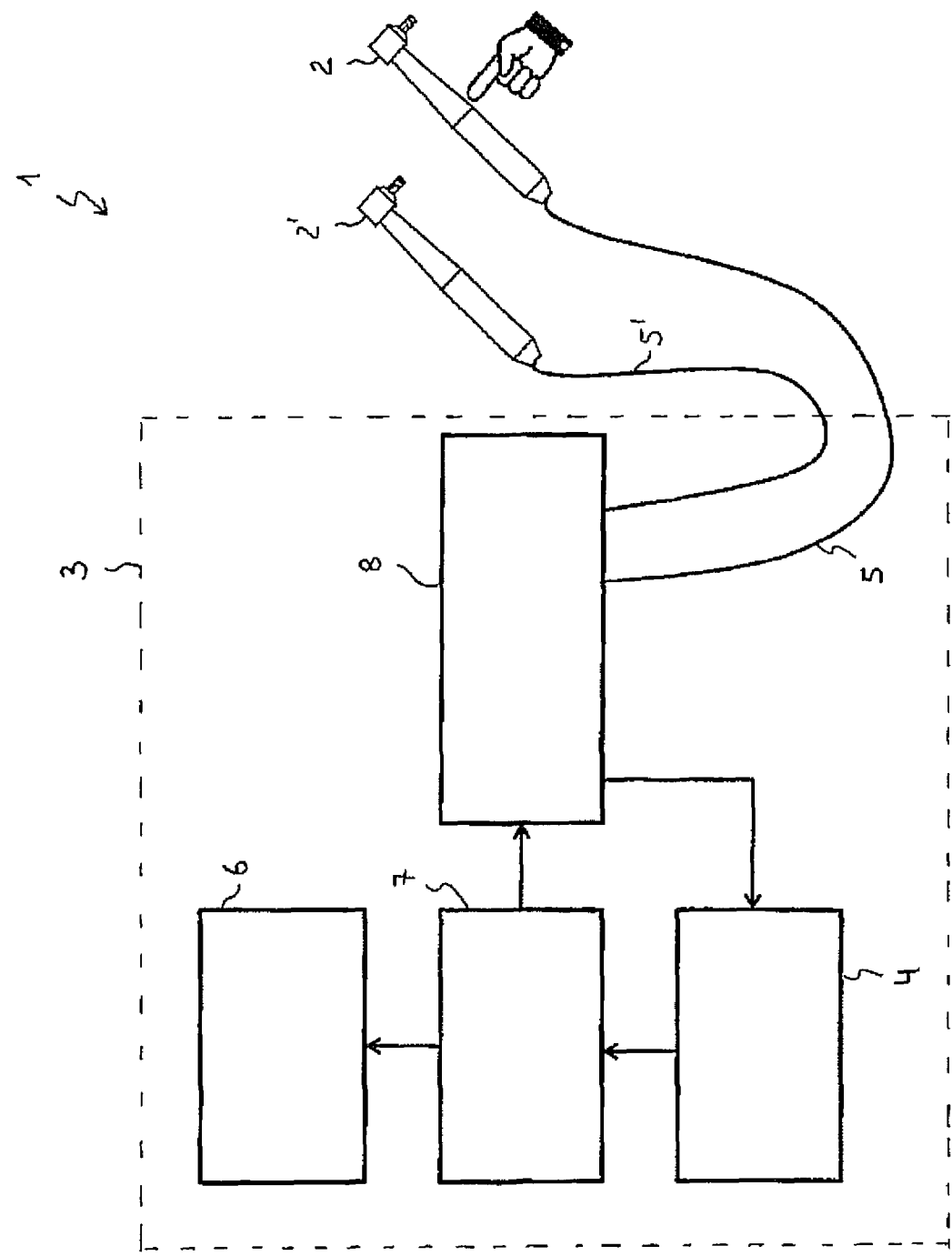
FIG. 1 shows a basic diagrammatic sketch of a dental treatment or examination instrument in accordance with the invention.

In FIG. 1 a diagrammatic sketch of a dental treatment or examination system 1 in accordance with the invention, also referred to as system 1 for short in the following, is shown. The system 1 can in particular be in the form of a dental treatment unit. The system 1 has a plurality of treatment or examination instruments 2, 2', also referred to as instruments 2, 2' for short in the following. The system 1 can have instrument-holders (not shown in the figures) for the instruments 2, 2' provided for storing the instruments 2, 2' during a period of time in which the instruments 2, 2' are not being used. The instrument-holder can, for example, be formed on a so-called dentist's element of the treatment unit. The instrument-holder is in this connection configured in such a way that the instruments 2 can easily be removed by a user of the system 1, that is, for example a dentist, merely with the use of one hand.

The instruments 2, 2' can, for example, include a dental electric-motor handpiece or a dental turbine, a dental camera, an ultrasound device, or an instrument operated by compressed air, etc.

Furthermore, the system 1 comprises a supply unit 3 which is coupled to the instruments 2, 2' and is configured in particular to supply the instruments 2, 2' with media, such as air and/or water and/or current, in particular by way of supply lines 5, 5', which are connected to the instruments 2, 2'. Moreover, the supply unit 3 is preferably configured to make available for the operation of the instruments 2, 2' activation or parameterization options for the instruments 2, 2'. Activation and parameterization options can be, for example, setting parameters, such as, for example, a motor speed in the case of an electric-motor handpiece. The making available of corresponding activation possibilities, as, for example, the setting of a motor speed with the aid of a so-called foot-actuated starting switch, also represents an initialization of the supply unit for the purposes of the invention.

Furthermore, the system 1 comprises means 4 to identify a contact of the instruments 2, 2', in particular contact by a human hand. In this connection, the system 1 is configured in such a way that the supply unit 3 is automatically initialized as a function of a contact of a selected instrument 2, identified by the means 4 for identification, for operation of the selected instrument and in this case, for example, makes available the activation or parameterization options and/or the media for the selected instrument 2. In particular, the configuration can be such that the supply unit 3 makes available the activation or parameterization options or the media for the relevant selected instrument 2 as soon as a contact of the relevant instrument 2 has been identified by the means 4 for identification. A user of the system 1 can thus select one of the instruments 2, 2' by merely contacting it; the system 1 is configured in such a way that such a contact of one of the instruments 2, 2' is identified by the means 4 for identification and as a consequence of this the activation or parameterization options and/or the media are made available by the supply unit 3 for the relevant instrument 2, that is, the instrument 2 selected by the contact.

In this way, it is possible to achieve a situation where the selected instrument 2—also referred to as "the" instrument 2 for short in the following—by means of the supply unit 3 is supplied with the media in a corresponding manner, or the activation or parameterization options are made available, as soon as a user of the system 1, that is, for example, the dentist, contacts the relevant instrument 2, that is, for example, removes it from the corresponding instrument-holder in order to work with the instrument 2. Corresponding selection of the instrument 2 and initialization of the supply unit 3 matched thereto for an operation of the instrument 2 are thus effected quasi automatically. Manipulation of the system 1 by the user going beyond this in order to select the instrument 2 is not necessary. As a result, in particular particularly intuitive operation of the system 1 by the user is rendered possible.

The measures for identifying the contact of an instrument shall be explained in greater detail in the following, where obviously these measures are then realized for a plurality of the instruments, ideally for all the instruments at the place of treatment.

The means 4 for identification of the contact preferably comprise a capacitive sensor. This is particularly well suited for detecting a contact of the instrument 2. In particular, in this way it is possible to avoid having a corresponding electromagnetic switch, as it is known from the prior art mentioned at the beginning, so that in comparison particularly cost-effective production is rendered possible.

For example, in this connection the configuration can, furthermore, be such that the means 4 for identifying the contact evaluate the capacitive coupling-in to a housing of the instrument 2 or to lines thereof, wherein the capacitive coupling-in is ascertained in particular by measuring ripple or interference voltages that increase significantly in the event of contact. As an alternative to this, the configuration can be such that the means 4 for the identification of the contact evaluate a change in capacitance of the instrument 2.

In general, suitable known methods, such as relaxation oscillators, charge-transfer methods, charge-time measurement or similar, can be used for the method of capacitance-measurement. The method of measuring the change in inherent capacitance is, however, preferred. The measurement of coupling capacitance would also be possible provided that there are two corresponding lines.

Particularly suitable capacitive identification is rendered possible if the means 4 for identification of the contact comprise an evaluation unit that is arranged in the supply unit 3 and is connected to the instrument 2 by way of a sensor line. The sensor line can, for example, be provided by a line specifically designed therefor; advantageously, however, it is formed by a current-supply line for the instrument 2 that is present anyway as such, that is, for example, by the above-mentioned supply line 5. In this case, it can be, for example, a motor-phase line or a line for the supply of current to a light source of the instrument 2.

In the example shown, the system 1 has, furthermore, a switching matrix 8 which is connected to the supply lines 5, 5' and also to the means 4 for the identification of the contact. In this case, the means 4 for the identification of the contact or the capacitive instrument-identification can be directly coupled, in the switching matrix 8, to that line of the supply lines 5 that is connected to the selected instrument 2. As soon as a contact of the instrument 2 is identified by the means 4, this is conveyed by the means 4 to a control unit 7 of the system 1. In the case of identification of a contact, the control unit 7 causes the activation or parameterization options or the media for the instrument 2 to be made available as soon as the contact has been identified. Making suitable media available can in this connection in particular also include making available a suitable supply current or the electrical connection of the selected instrument to a power or current-supply output of the control unit 7.

Furthermore, the supply unit 3 preferably has a display 6 or is connected to a display on which a presentation of operating parameters of the instrument 2 is effected, wherein the presentation is effected as a function of the identification of the contact of the instrument 2. In this connection, the configuration of the system 1 is, furthermore, preferably such that the display 6 is configured as an operator interface for setting operating parameters of the instrument 2, wherein in particular the activation or parameterization options are or can be indicated on the display 6.

In this case, whilst the motor of the instrument 2 is running preferably no contact-detection is effected. Put in more general terms, identification of the contact of the instrument 2 is preferably carried out merely in a non-activated state of the instrument 2. This is advantageous in particular because as a result it is guaranteed that the supply of media is not interrupted whilst working with the instrument 2.

In the example shown, the configuration is such that by means of the control unit 7 in accordance with the respective application the desired information, that is, for example, the parameterization options for the instrument 2, are indicated on the display 6. If then, for example, in the case of an electric-motor handpiece by way of a so-called foot-actuated starting switch (not shown in the figures) a start command is given for the instrument 2, by way of the switching matrix 8 the motor of the instrument 2 is connected to an output stage and started. As mentioned, then whilst the motor is running preferably no contact-detection is effected. After the motor of the instrument 2 has stopped, the switching matrix 8 is opened again, and the contact-detection is now active again. The current contact state is detected and conveyed to the control unit 7.

The method in accordance with the invention for operating the system 1 therefore includes the following steps
   (a) monitoring of a contact of the instruments 2, 2' and
   (b) initialization of the supply unit 3 for operation of the instrument, thus, for example, for making the activation or parameterization options or media available for one of the instruments 2 as a function of an identified contact of the one instrument 2.

In particular, the configuration can be such that all the relevant parameters or parameterization options are indicated on the display 6 and presented for editing as soon as the user contacts the instrument 2. As a result, a "touch-similar" operation is rendered possible for the instrument 2 without—as is the case in the prior art mentioned at the beginning—it being necessary in an elaborate manner to click through a menu or actuate a preselection switch. Thus a particularly comfortable operation is rendered possible.

The system 1 comprises two or even more corresponding instruments 2, 2'. In general, the system 1 can have any number of corresponding instruments 2, 2'.

Using the means 4 for identification it is automatically identified which of the instruments 2, 2' has been contacted, in which case the system 1 thereupon makes available for the contacted instrument 2 corresponding activation or parameterization options or the said media.

In FIG. 2a a sketch is shown of a possible configuration of the means 4 for identifying the contact. A case is shown in which n instruments 2, 2' are provided and for each of the n instruments 2, 2' one identification unit 41, 42 is formed in the means 4, that is, in total n identification means 41, 42 are formed from a first identification unit 41 to an nth identification unit 42. In this case, formed between each of the n identification units 41, 42, on the one hand, and the switching matrix 8, on the other hand, there is a respective signal-connection line 81, 82. The identification units 41, 42 are here configured so as to have a capacitive effect. In particular, therefore the n identification units 41, 42 can be configured as n capacitive sensors. In each case, a further signal-connection 71, 72 from each of the identification units 41, 42 to the control unit 7 is formed.

In FIG. 2b an alternative configuration is shown. The difference from the configuration according to FIG. 2a in this case consists merely in the fact that the identification units, here denoted as 41', 42', are formed as ripple-identification units.

Figure 3A:
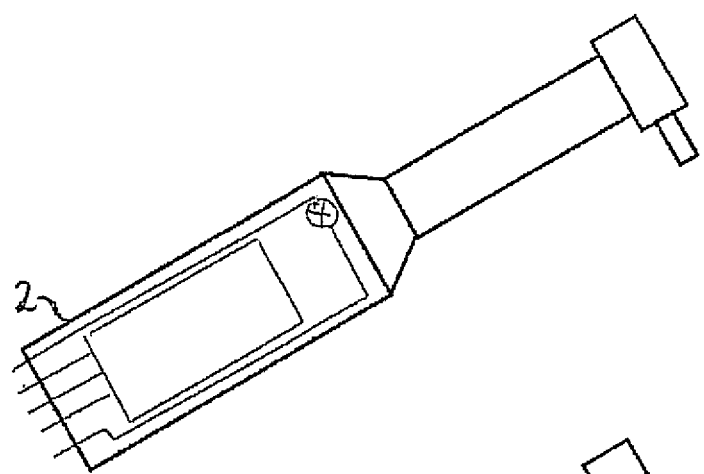
FIG. 3a shows a sketch of a possible embodiment of the instrument.
Figure 3B:
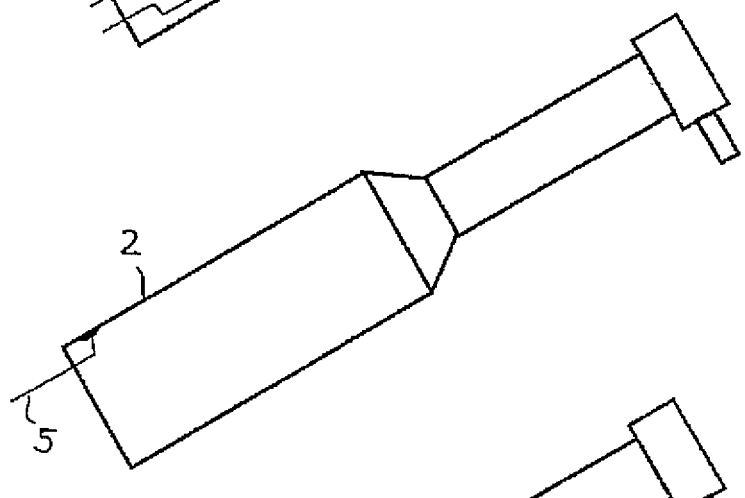
FIGS. 3b to 3d show sketches of further possible embodiments of the instrument.

In FIG. 3a a sketch is shown of a possible embodiment of the instrument 2. The sensor line is here a motor phase or a light-activation line or a line that is otherwise present. In the embodiment shown in FIG. 3b an explicit sensor line or one specifically designed for the identification is provided. The housing of the instrument 2 is configured so as to be conductive, or in the case of a plastics housing a capacitive coupling to the sensor line is formed.

Figure 3C:
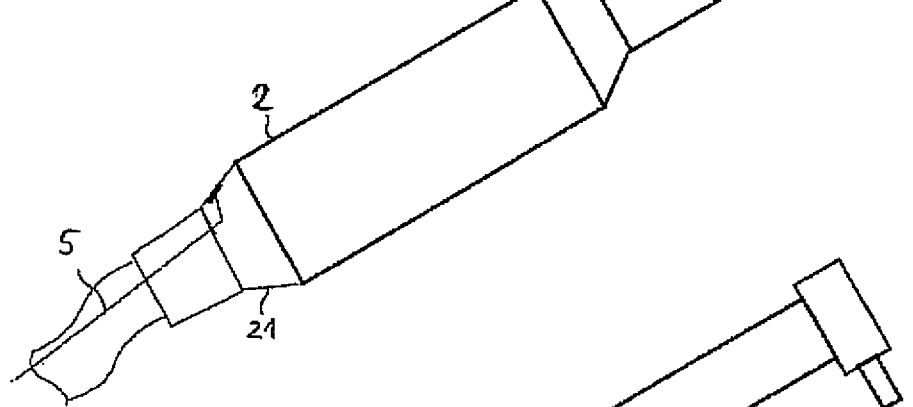

In the case of the embodiment sketched in FIG. 3c a sensor line is formed that ends in a connection piece 21 of the instrument 2. The housing of the instrument 2 and the connection piece are configured so as to be conductive, or in the case of a plastics housing a capacitive coupling is formed.

Figure 3D:
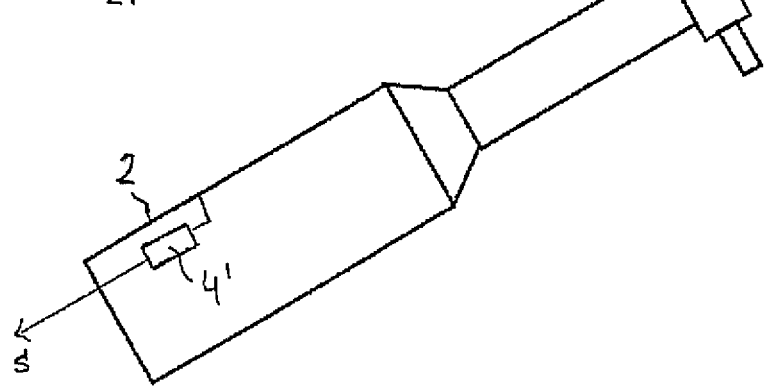

In the case of the embodiment shown in FIG. 3d the means 4 for identification or a corresponding identification unit 4', that is, for example, a capacitive sensor 4', are/is formed so as to be integrated into the instrument 2. When the instrument 2 is contacted, a signal S is sent from this identification unit 4' to the control unit 7.

In FIGS. 4a and 4b sketches are shown of a possible presentation on the display 6, FIG. 4a showing the case of the selection of the first instrument and FIG. 4b the case of the selection of the nth instrument.

Figure 5:
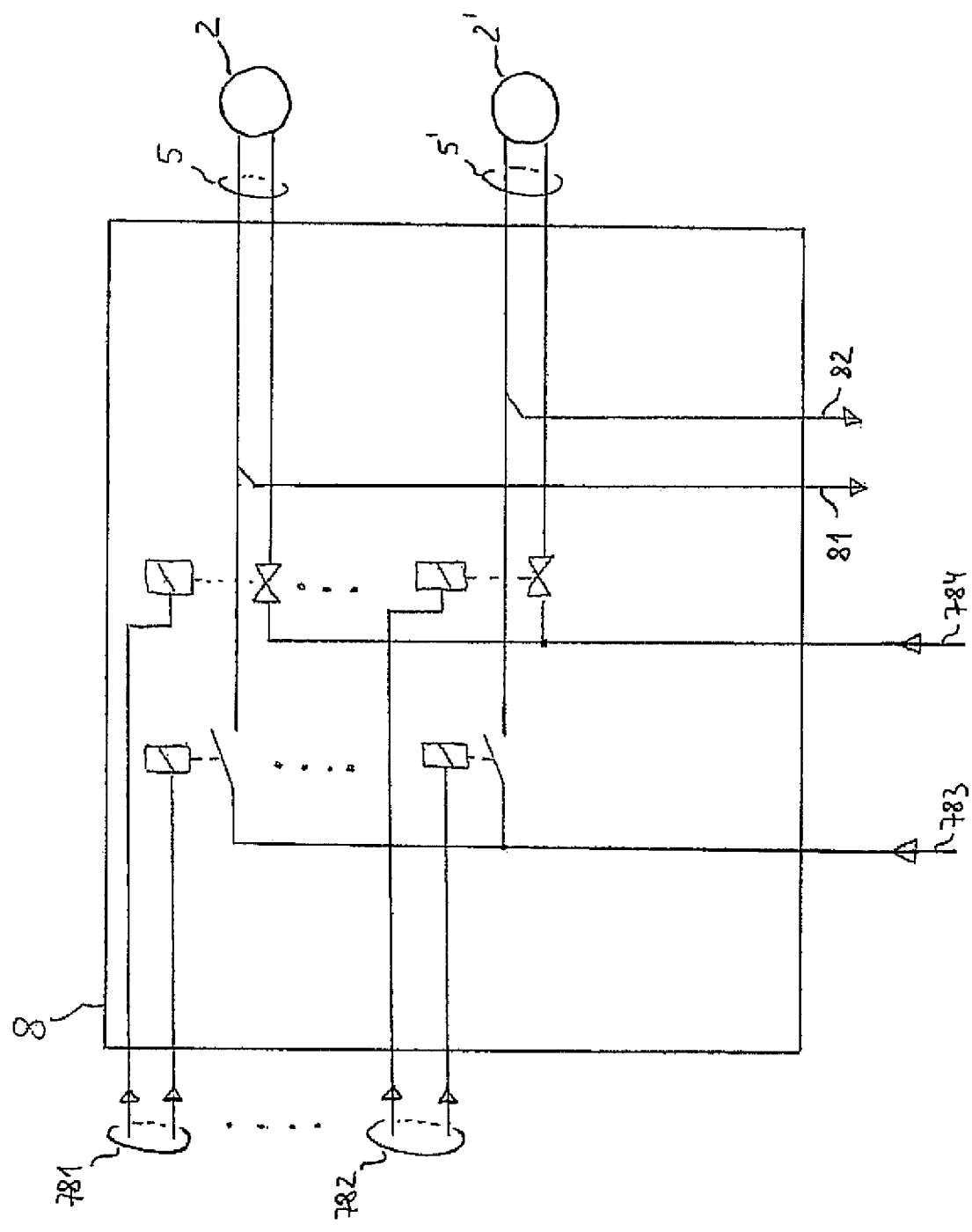
FIG. 5 shows a sketch of a possible embodiment of the switching matrix.

FIG. 5 shows a sketch of a possible embodiment of the switching matrix 8. Provided between each of the n instruments 2, 2' on the one hand and the switching matrix 8 on the other hand there is—as has already been described further above—a respective supply line 5, 5'. In the case where the first instrument 2 is contacted, a corresponding signal is sent from the switching matrix 8 by way of the signal-connection line 81 to the means 4 for identification of the contact; in the case where the nth instrument 2' is contacted, a corresponding signal is sent by way of the signal-connection line 82. If a corresponding identification unit is integrated in the relevant instrument, a touch signal is sent directly by way of the corresponding line 81 or 82 respectively.

Further n lines 781, 782 lead from the control unit 7 to the switching matrix 8; if the first instrument 2 is selected, a corresponding signal-transmission is effected by way of the line 781; if the nth instrument 2' is selected, a corresponding signal-transmission is effected by way of the nth line 782. Activation signals "light", "motor" etc. are sent to the switching matrix 8 by way of a further line 783. Finally, a media line 784 is used to supply air or water.

The invention claimed is:

1. A dental treatment or examination system comprising:
    a plurality of dental instruments;
    a supply unit;
    a plurality of sensor lines, each of the plurality of sensor lines electrically coupled to one of the plurality of dental instruments and the supply unit, and wherein each of the plurality of sensor lines consists of an existing electrical current-supply line associated with each of the plurality of dental instruments; and
    means to identify a contact of a selected dental instrument from the plurality of dental instruments, the means comprising at least one capacitive sensor measuring a capacitive coupling-in of the selected dental instrument, wherein the identification of the selected dental instrument is carried out when the plurality of dental instruments are in a non-activated state, and wherein the at least one capacitive sensor is electrically coupled to the sensor line associated with the selected dental instrument,
    wherein the system is configured to initialize, based upon the identified contact of the selected dental instrument, the supply unit for an operation of the selected instrument, the initialization including making activation or parameterization options available for the selected dental instrument,
    wherein the system is configured to operate the selected dental instrument in accordance with the activation or parameterization options, and
    wherein the supply unit includes a display configured to display operating parameters of the selected dental instrument wherein the operating parameters are displayed in response to the identification of the contact of the selected dental instrument.

2. The dental treatment or examination system according to claim 1, wherein the initialization of the supply unit further includes making fluid available.

3. The dental treatment or examination system according to claim 1, wherein the initialization of the supply unit further includes electrically coupling the selected dental instrument to a power output of a control unit.

4. The dental treatment or examination system according to claim 1, wherein the means for identifying the contact of the selected dental instrument evaluates a capacitive coupling in a housing of the selected dental instrument or to the sensor line coupled to the selected dental instrument.

5. The dental treatment or examination system according to claim 1, wherein the means for identifying the contact of the selected dental instrument comprises an evaluation unit that is arranged in the supply unit and is connected to the selected dental instrument by way of the sensor line coupled to the selected dental instrument.

6. The dental treatment or examination system according to claim 1, wherein the means for identifying the contact of the selected dental instrument is integrated into the selected dental instrument.

7. A method for operating a dental treatment or examination system having a plurality of dental instruments and a supply unit coupled to the plurality of dental instruments, the method comprising:
    monitoring the plurality of dental instruments,
    initializing, based upon an identified contact of a selected dental instrument of the plurality of dental instruments, the supply unit for an operation of the selected dental instrument, the initialization including making activation or parameterization options available for the selected dental instrument, wherein the identified contact is determined by a means comprising at least one capacitive sensor measuring a capacitive coupling-in of the selected dental instrument electrically coupled to a sensor line associated with the selected dental instrument, wherein the sensor line consists of an existing electrical current-supply line associated with the selected dental instrument, and wherein the identification of the selected dental instrument is carried out when the plurality of dental instruments are in a non-activated state; and
    activating the selected dental instrument based upon the activation or parameterization options,
    wherein the supply unit includes a display configured to display operating parameters of the selected dental instrument wherein the operating parameters are displayed in response to the identification of the contact of the selected dental instrument.

8. The method according to claim 7, wherein the initialization of the supply unit includes making fluid available.

9. The method according to claim 7, wherein the initialization of the supply unit includes electrically coupling the selected dental instrument to a power output of a control unit.

10. The method according to claim 7, wherein the capacitive sensor is located within at least one selected from the group consisting of a housing of the selected dental instrument or the sensor line connected to the selected dental instrument.

* * * * *